United States Patent
De Odorico et al.

(10) Patent No.: US 8,850,894 B2
(45) Date of Patent: Oct. 7, 2014

(54) METHOD AND DEVICE FOR ULTRASONIC TESTING OF A COMPONENT

(75) Inventors: Walter De Odorico, Kelkheim (DE); Roman Koch, Blankenbach (DE)

(73) Assignee: GE Sensing & Inspection Technologies GmbH (DE)

( * ) Notice: Subject to any disclaimer, the term of this patent is extended or adjusted under 35 U.S.C. 154(b) by 827 days.

(21) Appl. No.: 13/127,393

(22) PCT Filed: Nov. 3, 2009

(86) PCT No.: PCT/EP2009/064563
§ 371 (c)(1),
(2), (4) Date: Jul. 13, 2011

(87) PCT Pub. No.: WO2010/060758
PCT Pub. Date: Jun. 3, 2010

(65) Prior Publication Data
US 2011/0259105 A1    Oct. 27, 2011

(30) Foreign Application Priority Data
Nov. 3, 2008 (DE) .................. 10 2008 037 517

(51) Int. Cl.
*G01N 29/04* (2006.01)
*G01N 29/22* (2006.01)
*G01N 29/265* (2006.01)

(52) U.S. Cl.
CPC ........ *G01N 29/225* (2013.01); *G01N 2291/262* (2013.01); *G01N 29/265* (2013.01)
USPC ............................... 73/618; 73/866.5; 73/619

(58) Field of Classification Search
USPC ................. 73/618, 627, 570.5, 587, 649, 619
See application file for complete search history.

(56) References Cited

U.S. PATENT DOCUMENTS 1,464,103 A * 8/1923 Nash .............................. 367/130
4,167,880 A * 9/1979 George ........................... 73/644
(Continued)

FOREIGN PATENT DOCUMENTS

DE 10349948 B3 1/2005
JP S59222761 A 12/1984
(Continued)

OTHER PUBLICATIONS

Aviation Maintenance Technician Handbook General, 2008, Chapter 8, U.S. Department of Transportation, Federal Aviation Administration, Flight Standards Service.*
(Continued)

*Primary Examiner* — Peter Macchiarolo
*Assistant Examiner* — Samir M Shah
(74) *Attorney, Agent, or Firm* — GE Global Patent Operation; Mark A. Conklin

(57) ABSTRACT

A device and a method for ultrasonic testing by means of a local immersion technique of a stringer component section of a flat component are provided. The device includes a test head assembly mounted as moving floatingly by a holding device in the Y-direction longitudinally. The test head assembly includes: a test head that can be connected to an automatically actuated handling device and that can be moved by the handling device along the stringer; a test head holder; and a counter-holder coupled with the test head holder by an actuation element, wherein the actuation element is configured to steer the test head holder and the counter-holder from a closed position to an open position, the test head holder and the counter-holder being mounted floatingly along a guiding rail running in the X-direction transversely to the stringer, and fit, in a force-loaded manner, to each side surface of the stringer.

18 Claims, 4 Drawing Sheets

(56) References Cited

U.S. PATENT DOCUMENTS

| | | | |
|---|---|---|---|
| 4,229,796 A * | 10/1980 | Garrett | 702/39 |
| 4,279,158 A | 7/1981 | Kajiyama et al. | |
| 4,311,052 A * | 1/1982 | Jeffras et al. | 73/634 |
| 4,577,507 A | 3/1986 | Jestrich et al. | |
| 4,848,159 A | 7/1989 | Kennedy et al. | |
| 5,279,160 A * | 1/1994 | Koch | 73/643 |
| 5,567,881 A * | 10/1996 | Myers | 73/629 |
| 5,585,564 A * | 12/1996 | Brunty et al. | 73/634 |
| 6,220,099 B1 * | 4/2001 | Marti et al. | 73/633 |
| 6,234,025 B1 * | 5/2001 | Gieske et al. | 73/642 |
| 6,658,939 B2 * | 12/2003 | Georgeson et al. | 73/621 |
| 6,725,721 B2 * | 4/2004 | Venczel | 73/625 |
| 7,181,970 B2 * | 2/2007 | Haase et al. | 73/621 |
| 7,249,512 B2 * | 7/2007 | Kennedy et al. | 73/618 |
| 7,263,889 B2 * | 9/2007 | Kennedy et al. | 73/620 |
| 7,464,596 B2 * | 12/2008 | Bui et al. | 73/618 |
| 7,571,649 B2 * | 8/2009 | Young | 73/644 |
| 7,617,732 B2 * | 11/2009 | Bui et al. | 73/618 |
| 8,578,779 B2 * | 11/2013 | Bond-Thorley | 73/618 |
| 8,650,959 B2 * | 2/2014 | De Odorico et al. | 73/644 |
| 2002/0017140 A1 | 2/2002 | Georgeson et al. | |
| 2006/0162456 A1 * | 7/2006 | Kennedy et al. | 73/620 |
| 2006/0236769 A1 | 10/2006 | Tenley et al. | |
| 2006/0243051 A1 * | 11/2006 | Bui et al. | 73/618 |
| 2007/0044563 A1 * | 3/2007 | Sarr et al. | 73/618 |
| 2007/0044564 A1 * | 3/2007 | Bui et al. | 73/618 |
| 2007/0151375 A1 * | 7/2007 | Kennedy et al. | 73/866.5 |

FOREIGN PATENT DOCUMENTS

| | | |
|---|---|---|
| JP | 61275650 A | 12/1986 |
| JP | 62034047 A | 2/1987 |
| JP | 03084406 A | 4/1991 |
| JP | 04190157 A | 7/1992 |
| JP | 2009506328 A | 2/2009 |
| WO | 03065788 A2 | 8/2003 |
| WO | 2007025109 A2 | 3/2007 |

OTHER PUBLICATIONS

Unofficial English translation of JP Office Action dated Jan. 28, 2014 from corresponding JP Application No. 2011-533756.
Search Report and Written Opinion, dated Jan. 25, 2010.

* cited by examiner

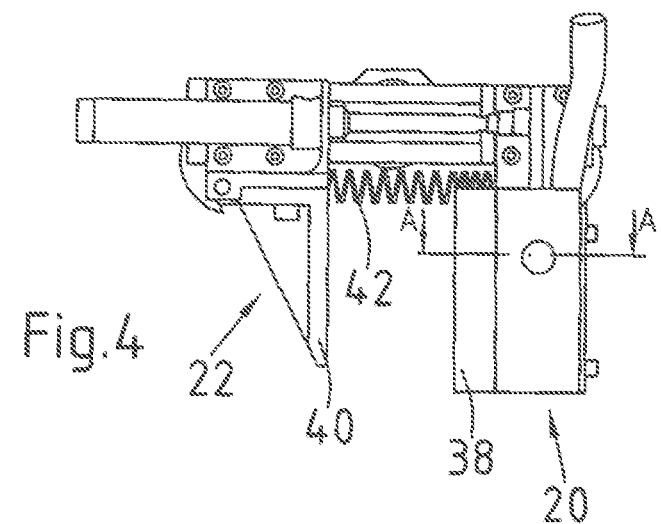
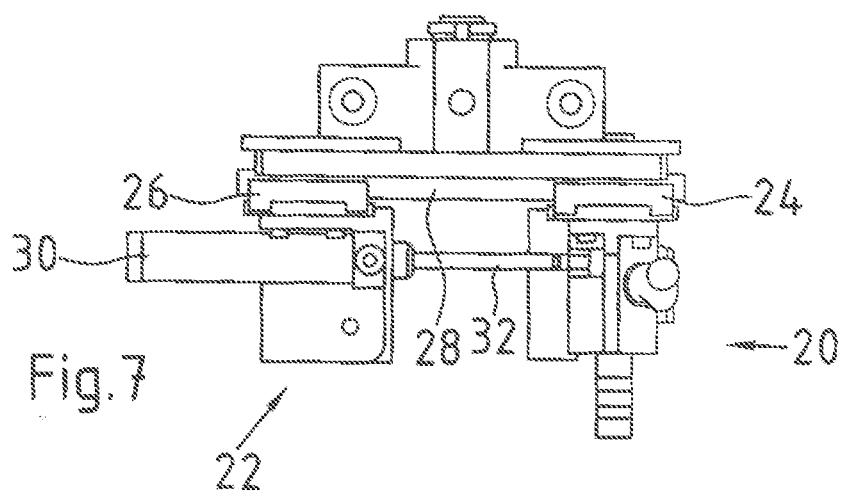
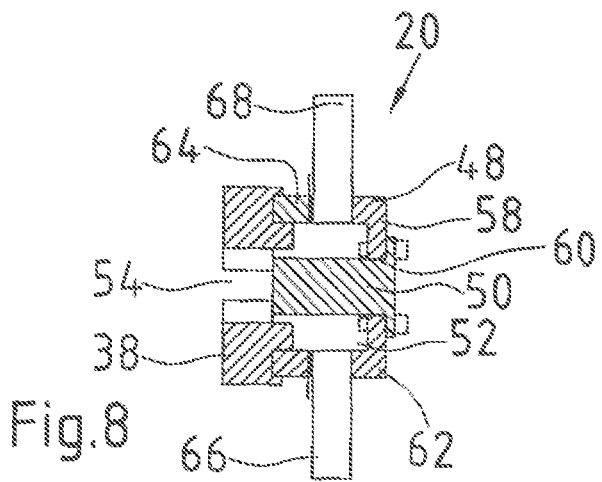

METHOD AND DEVICE FOR ULTRASONIC TESTING OF A COMPONENT

CROSS-REFERENCE TO RELATED APPLICATIONS

This application is a continuation of PCT International Application Serial Number PCT/EP2009/064563, filed on Nov. 3, 2009 and incorporated herein by reference in its entirety.

BACKGROUND OF THE INVENTION

1. Field of the Invention

Embodiments of the present invention is are related to a device and a method for ultrasound testing by means of local immersion technique of a stringer component section of a flat component.

2. Description of the Prior Art

A device as well as a method of the type mentioned above is described in patent US-A-2007/0044563. The device comprises a sensor holder which is designed to record one or several linear ultrasound sensors. The device lies on rollers on the flat component to be tested and is guided by an operator along the component section in the form of a band that is to be tested. The ultrasound sensors can be oriented in parallel or essentially in parallel to the surfaces to be tested, whereby the distance to the tested surface can be adjusted by means of an adjusting screw.

In the U.S. Pat. No. 7,464,596, a device for ultrasound testing of profiles, for example U-profiles, is described. The device comprises two sensor holders, of which at least one sensor holder is mounted in a mobile position along the guide rails, so that it can balance the oscillations of the profile to be tested.

An ultrasound sensor for testing of laminated structures, such as T or double-T profiles, is known from the U.S. Pat. No. 4,848,159. The device is designed in particular to detect errors in the radius area and in the surrounding areas of the laminated structure. The sensor comprises many sliders which are mounted in such a way as to guarantee a coordinated movement relative to the part to be tested. The holder comprises a great number of ultrasound transducers.

A method and a device for testing a component with a complex surface contour by means of ultrasound is described in patent DE-B-103 49 948. In this process a test head is moved by means of a multi-axial manipulator along a space curve at a distance in parallel to the surface of the tested component. Thereby the axle drives of a manipulator move synchronously along predetermined support points, whereby a trigger drive is moved in a synchronized manner, controlled with the axle drives and together with all axle drives in operation, according to a predetermined surface line reproducing the surface contour. The patent WO-A-03/065788 is related to a method and device for acoustic microscopy. The system comprises a controller and a "JIG," which is mounted removably on the tested object. The "JIG" comprises an acoustic transducer connected to the controller, which controls the position of the acoustic transducer. The "JIG" is adjusted in a way that enables the controller to move the acoustic transducer over the object and to adjust its position during the scans in order to compensate the contours of the scanned section of the object.

Requirements for the ultrasound testing of airplane structural components are particularly high. There is not only the requirement that large-area outer walls be tested, but also, preferably, the so-called longitudinal stiffening girders (stringers), which are mounted in the inside area of the component, should be subjected to ultrasound testing. In some cases, the longitudinal stiffening girders can be tested separately before their integration into another structural element.

With the introduction of fiber composite materials in the aircraft construction, it is also possible to manufacture large-surface components directly with the help of integrated longitudinal stiffening girders (stringers), so that they have to be tested in their end state, i.e. as an integrated unit.

A special challenge for ultrasound testing is the transition area between the longitudinal stiffening girder (stringer) and the stiffened surface of the structural element. This transition is described as a "foot," and poses a particular challenge for ultrasound testing, because this transition area is difficult to access in many cases.

In order to guarantee sufficient testing of this transition area as well as the stringer itself, a precise tracking control of the contour and gradient changes of the transition area and/or the profile of the stringer in the range of <1 mm by means of longitudinal extension of the stringer in the range of >5 m is necessary.

On the basis of the above requirements, until now ultrasound testing of this type of components was performed by means of manual testing because automatic testing, due to the difficult geometric and spatial characteristics, required very precise test head holders and guides, which are very expensive and complex.

Proceeding from this circumstance, embodiments of the present invention is based on a method and a device of the aforementioned type to be designed in such a way, so that this could be performed in a simple implementation form and with high speed.

SUMMARY OF THE INVENTION

One embodiment provides a method for ultrasonic testing by means of a local immersion technique of a stringer component section of a flat component with a device comprising a test head assembly mounted as moving floatingly by a holding device in the Y-direction longitudinally, the test head assembly comprising: a test head that can be connected to an automatically actuated handling device by the holding device; a test head holder; and a counter-holder, wherein the test head holder and the counter-holder are mounted floatingly along a guiding rail running in the X-direction transversely to the stringer component section. The method comprises: steering the test head holder and the counter-holder with an actuation element from a closed position to an open position such that the test head assembly is positioned by the handling device over the stringer component section to be tested; steering the test head holder and the counter-holder with the actuation element from the open position to the closed position, wherein the test head holder and the counter-holder are fitted by applied force to side surfaces of the stringer component section; and moving the test head assembly in a longitudinal direction to the stringer component section in a fully automated manner according to a preset dataset describing the course of the flat component and/or the stringer component section, wherein the contour changes of the stringer component section and/or the flat component are balanced by the test head holder and the counter-holder which move at least in the X and Y-directions.

In an alternate embodiment, a device for ultrasonic testing by means of a local immersion technique of a stringer component section of a flat component is provided. The device comprises: a test head assembly mounted as moving floatingly by a holding device in the Y-direction longitudinally, the test head assembly comprising: a test head that can be connected to an automatically actuated handling device by the holding device and that can be moved by the automatically actuated handling device along the stringer component section; a test head holder configured to receive the test head; and a counter-holder coupled with the test head holder by an actuation element, wherein the actuation element is configured to steer the test head holder and the counter-holder from a closed position to an open position, wherein the test head holder and the counter-holder are mounted floatingly along a guiding rail running in the X-direction transversely to the stringer component section, and fit, in a force-loaded manner, to each side surface of the stringer component section.

BRIEF DESCRIPTION OF THE DRAWINGS

Further details, advantages and characteristics of embodiments of the invention can be obtained from both the claims, the available characteristics, individually and/or in combination, and also from the following description of the figures of the available preferred implementations, in which:

FIG. 4 shows a front view of the test head assembly;

FIG. 7 shows a top view of the test head assembly; and

FIG. 8 shows a cross-section representation of a test head.

DETAILED DESCRIPTION OF THE INVENTION

Figure 1:
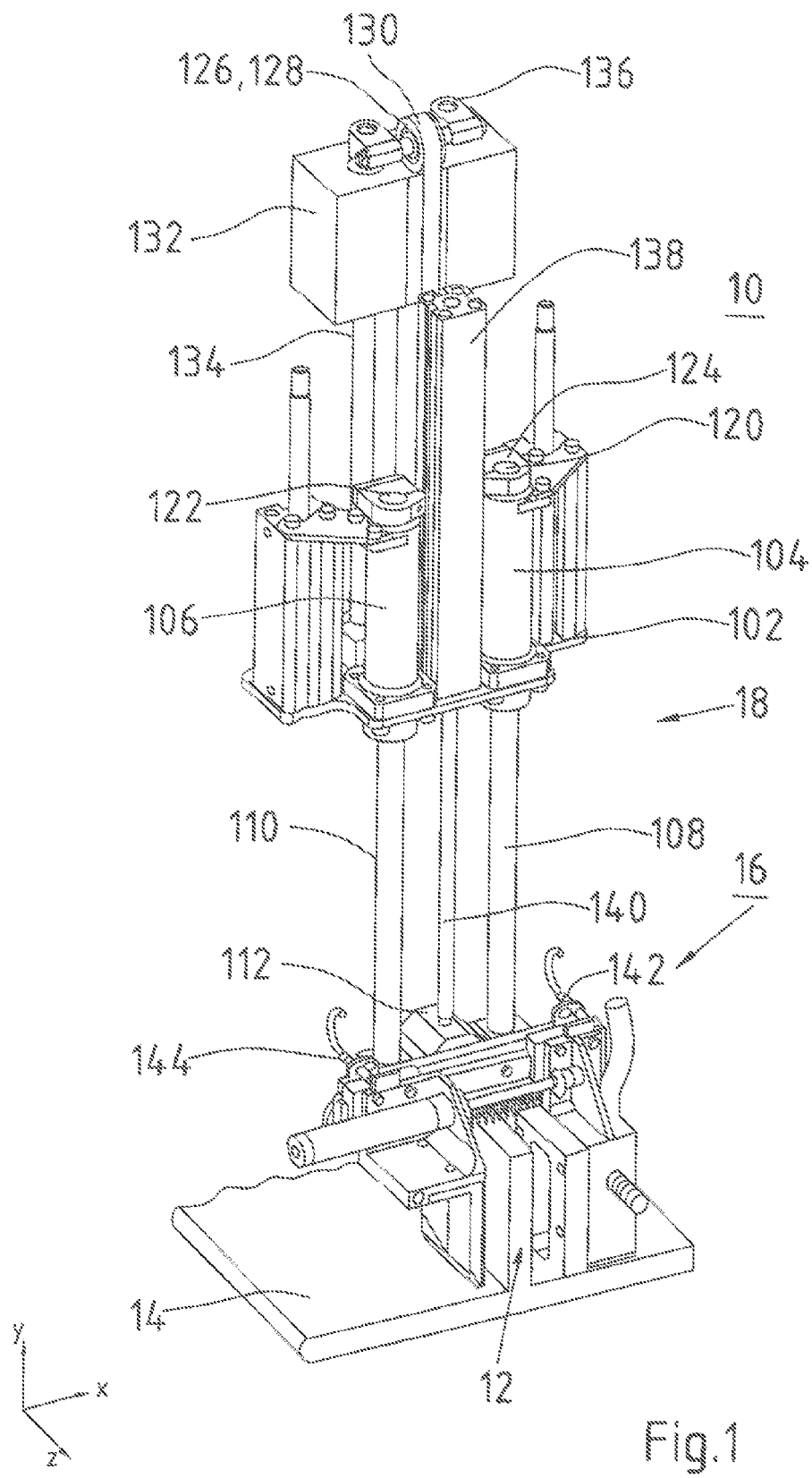
FIG. 1 shows a device for ultrasound testing of a component.
Figure 2:
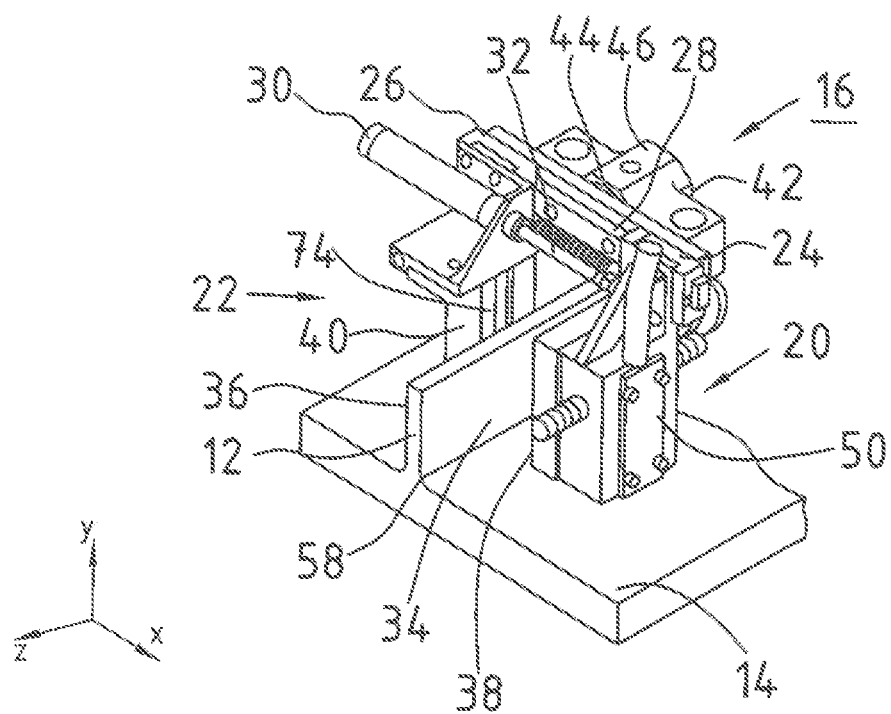
FIG. 2 shows a perspective view from the left of a test head assembly.
Figure 3:
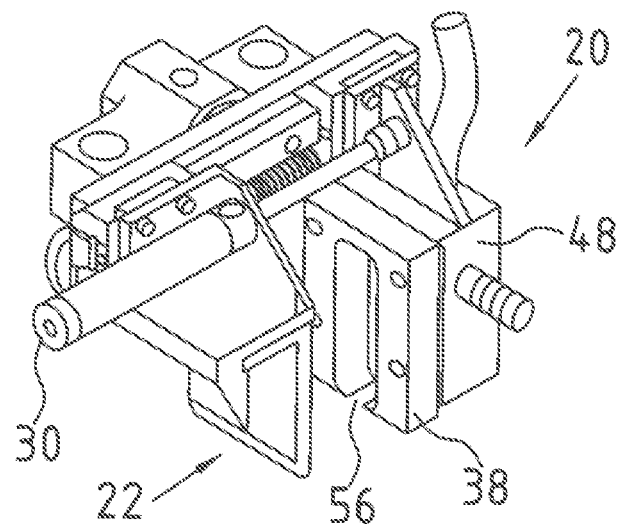
FIG. 3 shows a perspective view of the test head assembly according to FIG. 2 from the right-hand side.

FIG. 1 shows a device for ultrasound testing of a component section 12 such as a stringer, which, within a rectangular cartesian coordinate system as shown in FIG. 1, extends in the Y-direction from the surface lying in a X-Z plane (X-Z direction) of a flat component 14.

The data in FIG. 1 regarding the X-, Y- and Z axes are taken into account in the application.

The testing is performed by using a local immersion technique. The device 10 comprises a test head assembly 16, which can be moved by means of a holding device 18 as a gravitation-balancing device with a handling machine such as a portal robot (not shown) along the stringer 12. The test head assembly 16 is shown in details in FIGS. 2 to 8. The test head assembly 16 comprises a test head holder 20 as well as a counter-holder 22, which are mounted in a sliding position and can each be moved by guiding elements 24, 26 along a guiding rail in the X-direction, i.e. transversally to the longitudinal extension of the stringer 12. An actuation element, such as a pneumatic cylinder 30, is fixed on the counter-holder 22, which is coupled with the test head holder 20 by means of an actuation bar 32. By means of the pneumatic cylinder 30, the test head holder 20 as well as the counter-holder 22 can be steered from a first closed position to a second open position. The test head holder 20 as well as the counter holder 22 have, respectively, slide elements 38, 40 in the form of slide plates, which can move in parallel or essentially in parallel to each other and to the side surfaces 34, 36 of the stringer 12. In the second, open position, the slide plates 38, 40 are arranged at a certain distance from the side surfaces 34, 36. In this position, the test head assembly 16 can be positioned over the component section 12 that is to be tested.

By controlling the pneumatic cylinder 30, the test head assembly 16 can be steered from the second, open position to the first, closed position, in which the slide plates 38, 40 are lying spring-preloaded on the side surfaces 34, 36 of the stringer 12. To this purpose, the test head holder 20 and the counter-holder 22 are coupled to each other by means of a spring element 42 as a tension spring. The guide rail 28, along which the test head holder 20 and the counter-holder 22 are arranged in a shifting position, is connected by means of a swivel 44 with a connecting block 46 of the gravitation-balancing device 18. The swivel 44 permits a swinging of rotational movement of the test head assembly 16 around an axis running in longitudinal direction (Z-direction) of the stringer 12. By means of the gravitation-balancing device 18, a floating suspension of the test head assembly in the Y-direction is implemented. By means of the characteristics described above, an advantage is achieved, which permits the test head assembly 16 to be moved with several levels of freedom, whereby by means of the spring-preloaded holders 20, 22 fitted at the side surfaces 34, 36 of the stringer 12 an adaptation to the contour changes of the stringer 12 takes place, and whereby by means of the floating suspension of the holders 20, 22 along the guiding rail 28, the course changes of the stringer 12 in the X-direction, i.e. transversally to the longitudinal extension of the stringer 12 are balanced, and whereby the changes in the tilt of the stringer 12 can be balanced by means of the rotary bearing element 44. The test head holder 20 comprises, preferably, a metal base body 48 for receiving the test head 50, as a phased-array test head with sending and receiving elements, as well as the slide plate 38. The base body 48 is built essentially in the form of a cuboid, with a hollow space 52, which forms a water chamber. The chamber 52 is covered on one open side of the base body 48 by the slide plate 38, which comprises a slit-like opening 54 as a water outlet opening running in the Z-direction. The slit-like opening is open to a surface running in the X-Z plane of the component 14 and has a slit-like opening 56 there. This allows a transition area between the stringer 12 and the flat component 14, described as "foot," to be tested by means of the phased-array test head 50.

In a wall 58, which is positioned against the slide plate 38, the base body 48 has a slit-like opening 60, in which the test head 50 is fitted and which is extended within the water chamber 50 up to the slide plate 38. In the side walls 62, 64, which essentially run under a right angle to the front wall 58 and the slide plate 38, water inlet connections 66, 68 are mounted, which lead to the water chamber 52.

Figure 5:
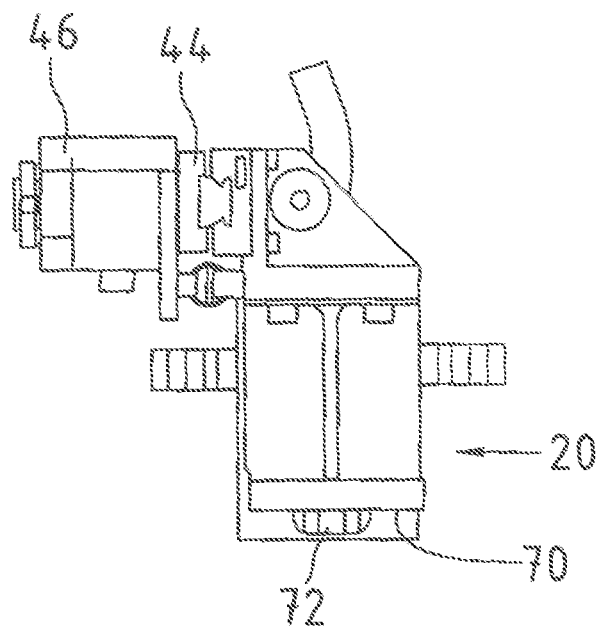
FIG. 5 shows a side view of the test head assembly.

In the lateral view according to FIG. 5, it can be seen that on the bottom side 70 of the test head holder 20 supporting and guiding elements 72 are mounted as roller elements, through which the test head assembly 16 can move over the surface of the component 14.

As is known, the device operates by means of local immersion technique. Through the water inlets 66, 68, water is flushed in the water chamber 52, which is then led through the slit-like opening 54 against the side surface 34 of the stringer 12. The longitudinal extension of the slit-like opening 54 in the Y-direction is longer than the height of the stringer 12, so that the water, which comes out of the slit-like opening 54, fills both an intermediate space, formed between the slide plate 40 of the counter-holder 22 and the side surface 36, and also an intermediate space formed between the slide plate 38 and the side surface 34, in order to achieve an adequate coupling of the ultrasound waves. For better distribution of the water, furrows or grooves 74 for distribution of the water extended in the Y-direction are provided in the slide plate 40 of the counter-holder 22.

Figure 6:
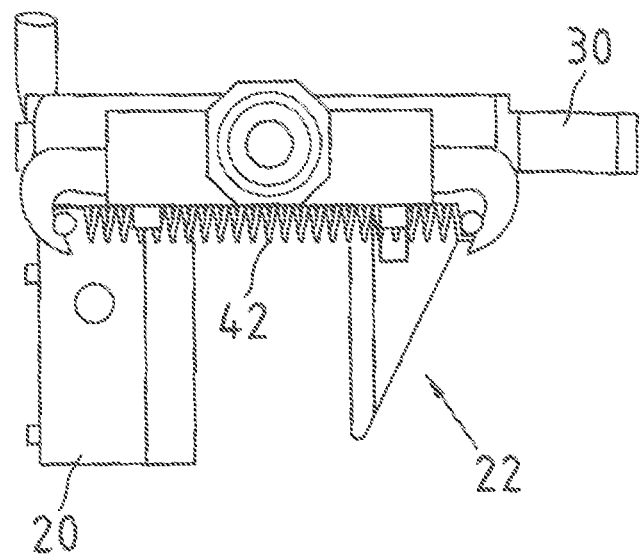
FIG. 6 shows a rear view of the test head assembly.

Another feature of the counter-holder 22 is characterized in that it runs pointedly to the fin base 58, as shown in FIG. 6. In this way, the testing of stringers 12, which run in a tilted position with respect to the component 14, is also enabled. In order to balance the height differences of the component 12 in the Y-directions, the test head assembly 16 and the gravitation-balancing device 18 are guided along the stringer 12 that is to be tested. The gravitation-balancing device 18 comprises a base plate 102, which can be connected firmly with a handling device, such as portal robot (not shown). The guiding cylinders 104, 106, which are arranged in parallel to each other and at a certain distance between them, extend from one top side of the base plate 102. The guiding bars 108, 110 are bearing-suspended in axially shifting position in the guiding cylinders 104, 106. The first, bottom ends of the guiding bars 110, 108, which extend under the base plate 102, are connected to each other by means of the connecting block 112. The swivel 44, to which the test head assembly 16 is fixed, is mounted in the connecting block. The first, top ends 120, 122 of the guiding bars 110, 108, which extend above the base plate 102, are also connected to each other by means of the connecting block 124. The connecting element 124 is connected with a closed belt 130, which is led through a first guide pulley 126 and a second guide pulley 128 (not shown). Furthermore, the belt is coupled to a gravitation counterweight 132, which slides along the guiding bars 134, 136 in opposition to the movement of the test head 10. The ends of the guiding bars 134, 136 are connected to each other by means of an axle, on which the first guide pulley 126 is positioned revolvably between the guiding bars. The second guide pulley 128 is mounted in a revolvable manner in the base plate 102.

Furthermore, the base plate 110 has a pneumatic cylinder 138, preferably between the guiding bars 110, 108, whereby a piston rod 140 of the pneumatic cylinder 138 is connected with the connecting block 112, in order to adjust the test head 10 in work position.

In order to guarantee that the test head is always lying on a side surface of the component section to be tested, it is ensured that the test head assembly has one test head holder receiving the test head, as well as a counter-holder, that the test head holder as well as the counter-holder are suspended along a guide rail running in the X-direction transversely to the component section in a moving or floating state and are lying in a spring-preloaded position on one side surface of the component section. The guide rail may be mounted with a capability for a rotational movement around an axis running in the Z-direction.

Furthermore, the test head assembly may be suspended moving high in the Y-direction over the holding device built as a gravitation-balancing device, preferably in a floating position.

An actuation element such as a pneumatic cylinder may be provided to control the counter-holder and the test head holder.

In order for the test head holder to lie in a spring-preloaded manner on the side surface of the component to be tested, the test head holder and the counter holder may be coupled with each other by means of a spring element such as a tension spring.

The end positions of the test head holder and the counter-holder may be recorded by an end switch such as a proximity switch.

The test head holder and the counter-holder may each have a slide plate clinging to the side surface of the component section, whereby the slide plate of the test head holder has a slit-like opening with a hole on the top side, which is extended in the Y-direction, whereby the height dimension (Y-direction) of the slit-like opening is larger than the height of the component section and that the slide plate of the counter-holder has grooves running in the Y-direction.

The slide plates or the slide elements may be made of plastic.

In order to simplify the movement of the test head assembly along the component to be tested, the test head holder may have, on its bottom side, a supporting and guiding element, such as a roller, for supporting and guiding the component to be tested.

The test head holder may have a base body with a cuboid form, comprising a metal base body, with a milling groove that forms a water chamber, which is covered by the slide plate, whereby in one of the walls opposite to the slide plate a recess for receiving the test head is built and whereby in the side walls of the base body intakes are mounted which lead to the water chamber.

A method for testing of, in particular, the stringer 12 of the flat component 14 is characterized in that the test head holder 20 and the counter-holder 22 are arranged first in an open position over the component section 12. After a safety check by querying the limit switches, which check the end positions of the test head holders 20 as well as of the counter-holders 22, the water inlet is opened and the test head assembly 16 is replaced by the handling machine over the component section 12.

By controlling the pneumatic cylinder, the test head holder 20 and the counter-holder 22 are steered into the closed position, so that the holders 20, 22 are fitted spring-preloaded on the side surfaces 34, 36.

Next, the test head assembly is moved in the direction (Z-direction) along stringer 12 and measurement values are taken, whereby the ultrasound testing is performed, preferably by using the amplitude-runtime local curve method (ALOK method) and/or alternatively combined with the standard clearance evaluation.

The methods according to embodiments of the invention achieve a situation where the test head holder and/or the test head, which are moved by the handling machine, are suspended in a movable position with several levels of freedom in relation to the component and/or the component section. In this way, the test head can follow minimal course alterations or contour changes of the component or the component section, without a need for the handling machine to perform corresponding corrective movements.

A time-consuming setup of the device is eliminated, and compared to manual testing, very fast, reproducible and automated testing is achieved. Since the control is alleviated, the testing as a whole can be performed faster.

By the implementation of the test head assembly as a test head holder and a counter-holder, a bracket-like configuration is obtained, with which the test head is always in contact with the side surface of the component to be tested.

According to an alternate embodiment, an intermediate space formed between the test head holder and the counter-holder and oriented towards the component section is completely overflown by water flowing from the test head holder.

In this way, a local immersion technique is implemented. To compensate for the changes in the height of the component to be tested, the test head assembly is guided by a gravitation-balancing device. The measurement values obtained by the test head are preferably recorded and evaluated by means of an amplitude-runtime local curve method (ALOK method) and/or standard clearance evaluation. As a result of embodiments of the present invention, on the one hand, of the test head assembly and, on the other hand of the suspension by means of a gravitation balancing device, testing speeds are possible in the range of 100 mm/s to 500 mm/s, preferably 200 mm/s, in longitudinal direction.

What is claimed is:

1. A method for ultrasonic testing by means of a local immersion technique of a stringer component section of a flat component with a device comprising a test head assembly mounted as moving floatingly by a holding device in a Y-direction longitudinally, the test head assembly comprising: a test head that can be connected to an automatically actuated handling device by the holding device; a test head holder; and a counter-holder, wherein the test head holder and the counter-holder are mounted floatingly along a guiding rail running in an X-direction transversely to the stringer component section, the method comprising:

steering the test head holder and the counter-holder with an actuation element from a closed position to an open position such that the test head assembly is positioned by the handling device over the stringer component section to be tested;

steering the test head holder and the counter-holder with the actuation element from the open position to the closed position, wherein the test head holder and the counter-holder are fitted by applied force to side surfaces of the stringer component section; and moving the test head assembly in a longitudinal direction to the stringer component section in a fully automated manner according to a preset dataset describing the course of the flat component and/or the stringer component section, wherein the contour changes of the stringer component section and/or the flat component are balanced by the test head holder and the counter-holder which move at least in the X and Y-directions.

2. A method according to claim 1, wherein the test head assembly is mounted with a capability for rotational movement around an axis running in a Z-direction.

3. A method according to claim 1, wherein the test head holder and the counter-holder are steered with a pneumatic system in the open position and with a spring force in the closed position.

4. A method according to claim 1, further comprising flooding an intermediate space between the test head holder and the counter-holder with water flowing from the test head holder.

5. A method according to claim 1, wherein the test head assembly is moved with a gravitation-balancing device.

6. A method according to claim 1, wherein measurements taken by the test head are recorded and evaluated by an amplitude-runtime local curve method (ALOK method) and/or standard clearance evaluation.

7. A method according to claim 1, wherein the test head assembly is moved with a speed in the range from 100 mm/s to 500 mm/s in the longitudinal direction.

8. A method according to claim 1, wherein the test head assembly is moved with a speed of 200 mm/s in the longitudinal direction.

9. A device for ultrasonic testing by means of a local immersion technique of a stringer component section of a flat component, the device comprising:

a test head assembly mounted as moving floatingly by a holding device in a Y-direction longitudinally, the test head assembly comprising:

a test head that can be connected to an automatically actuated handling device by the holding device and that can be moved by the automatically actuated handling device along the stringer component section;

a test head holder configured to receive the test head; and a counter-holder coupled with the test head holder by an actuation element, wherein the actuation element is configured to steer the test head holder and the counter-holder from a closed position to an open position, wherein the test head holder and the counter-holder are mounted floatingly along a guiding rail running in an X-direction transversely to the stringer component section, and fit, in a force-loaded manner, to each side surface of the stringer component section.

10. A device according to claim 9, wherein the test head assembly and/or the guiding rail is/are mounted on the holding device and can rotate around an axis running in a Z-direction.

11. A device according to claim 9, wherein the holding device comprises a gravitation-balancing device.

12. A device according to claim 9, wherein the actuation element comprises a pneumatic cylinder.

13. A device according to claim 9, wherein the test head holder and the counter-holder are coupled to each other with a spring element.

14. A device according to claim 9, wherein a limit switch is assigned to the test head holder and the counter-holder, respectively, as a proximity switch.

15. A device according to claim 9, wherein the test head holder and the counter holder comprise slide plates fitting on the side surfaces of the stringer component section, wherein the slide plate of the test head holder has a slit-like opening extending in the Y-direction, and a top-side opening, the height extension of the slit-like opening being larger than the height of the stringer component section, and wherein the slide plate of the counter-holder comprises grooves running in the Y-direction.

16. A device according to claim 15, wherein the slide plates are made of plastic.

17. A device according to claim 9, wherein the test head holder comprises supporting and guiding elements, wherein the supporting and guiding elements are configured to support and guide the component.

18. A device according to claim 9, wherein the test head holder comprises a cuboidal metal base body, the base body comprising:

a milling groove which forms a water chamber that is covered by a slide plate, wherein the water chamber comprises a wall positioned opposite to the slide plate comprising a recess configured to receive the test head, and inlets arranged in the side walls of the base body leading into the water chamber.

* * * * *